(12) United States Patent
Kim et al.

(10) Patent No.: US 9,005,952 B2
(45) Date of Patent: *Apr. 14, 2015

(54) MICROORGANISM PRODUCING L-METHIONINE PRECURSOR AND THE METHOD OF PRODUCING L-METHIONINE PRECURSOR USING THE MICROORGANISM

(75) Inventors: Chul Ha Kim, Seoul (KR); So Young Kim, Gyeonggi-do (KR); Young Uk Shin, Gyeonggi-do (KR); Hye Won Um, Gyeonggi-do (KR); Jin Sook Chang, Seoul (KR); Young Wook Cho, Seoul (KR); Han Jin Lee, Seoul (KR); In Kyung Heo, Seoul (KR); Chang Il Seo, Incheon (KR); Kwang Ho Na, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 439 days.

This patent is subject to a terminal disclaimer.

(21) Appl. No.: 12/062,835

(22) Filed: Apr. 4, 2008

(65) Prior Publication Data

US 2009/0253186 A1   Oct. 8, 2009

(51) Int. Cl.

| | | |
|---|---|---|
| C12P 13/12 | (2006.01) |
| C12N 1/00 | (2006.01) |
| C12N 15/00 | (2006.01) |
| C12N 1/20 | (2006.01) |
| C12N 9/04 | (2006.01) |
| C12N 9/10 | (2006.01) |
| C12Q 1/68 | (2006.01) |
| C07H 21/04 | (2006.01) |
| C12N 9/12 | (2006.01) |
| C12P 13/06 | (2006.01) |
| C12R 1/19 | (2006.01) |

(52) U.S. Cl.
CPC ........... *C12N 1/20* (2013.01); *C12N 9/0006* (2013.01); *C12N 9/1029* (2013.01); *C12N 9/1217* (2013.01); *C12P 13/06* (2013.01); *C12P 13/12* (2013.01); *C12R 1/19* (2013.01)

(58) Field of Classification Search
CPC .... C12N 9/1029; C12N 9/1217; C12N 9/006; C12N 9/1085; C12N 15/70; C12P 13/06
See application file for complete search history.

(56) References Cited

U.S. PATENT DOCUMENTS

| | | | |
|---|---|---|---|
| 7,238,502 B2* | 7/2007 | Kroger et al. ................. 435/113 |
| 8,283,152 B2* | 10/2012 | Kim et al. ................. 435/252.33 |
| 2002/0049305 A1 | 4/2002 | Bathe et al. |
| 2003/0092026 A1 | 5/2003 | Rey et al. |
| 2005/0054060 A1 | 3/2005 | Chateau et al. |
| 2006/0003425 A1* | 1/2006 | Kroger et al. ................. 435/113 |
| 2010/0184164 A1 | 7/2010 | Kim et al. ..................... 435/113 |

FOREIGN PATENT DOCUMENTS

| | | |
|---|---|---|
| JP | 2000-139471 | 5/2000 |
| KR | 19920008365 B1 | 9/1992 |
| WO | 2004/069996 A | 8/2004 |
| WO | 2005/075625 A1 | 8/2005 |
| WO | 2005108561 A2 | 11/2005 |
| WO | 2007/012078 A | 1/2007 |
| WO | 2007-077041 A1 | 7/2007 |
| WO | 2008013432 A1 | 1/2008 |
| WO | 2008-127240 A1 | 10/2008 |

OTHER PUBLICATIONS

Hwang et al. *Corynebacterium glutamicum* utilizes both trans-sulfuration and direct sulfhydrylation pathways for methionine biosynthesis. J Bacteriol. Mar. 2002;184(5):1277-86.*
Mischoulon et al., Role of S-adenosyl-L-methionine in the treatment of depression: a review of the evidence, American Journal of Clinical Nutrition, 2002, vol. 76, pp. 1158S-1161S.
Mato et al., S-Adenosylmethionine: a control switch that regulates liver function, FASEB, 2002, vol. 16(1), pp. 15-26.
Biran et al., Control of methionine biosynthesis in *Escherichia coli* by proteolysis, Molecular Microbiology, 2000, vol. 37(6), pp. 1436-1443.
Kromer et al., Accumulation of homolanthionine and activation of a novel pathway for isoleucine biosynthesis in *Corynebacterium glutamicum* McbR deletion strains, Journal of Bacteriology, 2006, vol. 188(2), pp. 609-618.
Jensen et al., Artificial promoters for metabolic optimization, Biotechnology and Bioengineering, 1998, vol. 58(2-3), pp. 191-195.
Carrier et al., Library of synthetic 5' secondary structures to manipulate mRNA stability in *Escherichia coli*, Biotechnology Progress, 1999, vol. 15, pp. 58-64.
Franch et al., U-turns and regulatory RNAs, Current Opinion in Microbiology, 2000, vol. 3, pp. 159-164.
Qiu et al., The *Escherichia coli* polB locus is identical to dinA, the structural gene for DNA polymerase II, The Journal of Biological Chemistry, 1997, vol. 272(13), pp. 8611-8617.
Yano et al., Directed evolution of an aspartate aminotransferase with new substrate specificities, Proceedings of the National Academy of Science, USA, 1998, vol. 95, pp. 5511-5515.
Wente et al., Different amino acid substitutions at the same position in the nucleotide-binding site of aspartate transcarbamoylase have diverse effects on the allosteric properties of the enzyme, The Journal of Biological Chemistry, 1991, vol. 266(31), pp. 20833-20839.
Belfaiza et al., Direct sulfhydrylation for methionine biosynthesis in *Leptospira meyeri*, Journal of Bacteriology, 1998, vol. 180(2), pp. 250-255.

(Continued)

*Primary Examiner* — Yong Pak
(74) *Attorney, Agent, or Firm* — Seed IP Law Group PLLC

(57) ABSTRACT

The present invention relates to a microorganism producing L-methionine precursor, O-acetylhomoserine, and a method of producing L-methionine precursor using the microorganism.

21 Claims, 3 Drawing Sheets

(56) References Cited

OTHER PUBLICATIONS

Villaverde et al., Fine regulation of cI857-controlled gene expression in continuous culture of recombinant *Escherichia coli* by temperature, Applied and Environmental Microbiology, 1993, vol. 59(10), pp. 3485-3487.

GenBank Accession No. AAL90885, Mar. 19, 2002, 1 page.

GenBank Accession No. NP_294596, Dec. 3, 2007, 2 pages.

Ruckert et al., "Genome-wide analysis of the L-methionine biosynthetic pathway in *Corynebacterium glutamicum* by targeted gene deletion and homologous complementation," *Journal of Biotechnology* 104:213-228, 2003.

Vitreschak et al., "Attenuation regulation of amino acid biosynthetic operons in proteobacteria: comparative genomics analysis," *FEMS Microbiology Letters* 234:357-370, 2004.

NCBI Reference Sequence: NP_249081 homoserine O-acetyltransferase [*Pseudomonas aeruginosa* PA01], 2009.

Q9RVZ8 homoserine O-acetyltransferase [*Deinococcus radiodurans* R1], 2009.

YP_886028 homoserine O-acetyltransferase [*Mycobacterium smegmatis* str. MC2155], 2009.

Gophna, et al., Evolutionary plasticity of methionine biosynthesis, Gene, 2005, 355:48-57.

Andersen, et al., Molecular characterization and sequence of a methionine biosynthetic locus from *Pseudomonas methionine*, Journal of Bacteriology, 1998, 180(17):4497-4507.

UNITPROT: Q8RMX0, 2002.

Kromer, et al., Metabolic pathway analysis for rational design of L-methionine production by *Escherichia coli* and *Corynebacterium glutamicum*, Metabolic Engineering, 2006, 8(4):353-369.

* cited by examiner

SEQUENCE LISTING

<160> NUMBER OF SEQ ID NOS: 34

<210> SEQ ID NO 1
<211> LENGTH: 70
<212> TYPE: DNA
<213> ORGANISM: Artificial Sequence
<220> FEATURE:
<223> OTHER INFORMATION: primer for amplification of Chloramphenichol

<400> SEQUENCE: 1

TTACTCTGGT GCCTGACATT TCACCGACAA AGCCCAGGGA ACTTCATCAC gtgtaggctg    60

Gagctgcttc    70

<210> SEQ ID NO 2
<211> LENGTH: 70

```
<212> TYPE: DNA
<213> ORGANISM: Artificial Sequence
<220> FEATURE:
<223> OTHER INFORMATION: primer for amplification of Chloramphenichol

<400> SEQUENCE: 2

TTACCCCTTG TTTGCAGCCC GGAAGCCATT TTCCAGGTCG GCAATTAAAT catatgaata      60

Tcctccttag                                                            70

<210> SEQ ID NO 3
<211> LENGTH: 70
<212> TYPE: DNA
<213> ORGANISM: Artificial Sequence
<220> FEATURE:
<223> OTHER INFORMATION: primer for amplification of kanamycin

<400> SEQUENCE: 3

AAAGAATATG CCGATCGGTT CGGGCTTAGG CTCCAGTGCC TGTTCGGTGG gtgtaggctg      60
gagctgcttc                                                            70

<210> SEQ ID NO 4
<211> LENGTH: 70
<212> TYPE: DNA
<213> ORGANISM: Artificial Sequence
<220> FEATURE:
<223> OTHER INFORMATION: primer for amplification of kanamycin

<400> SEQUENCE: 4

AGACAACCGA CATCGCTTTC AACATTGGCG ACCGGAGCCG GGAAGGCAAA catatgaata      60
tcctccttag                                                            70

<210> SEQ ID NO 5
<211> LENGTH: 71
<212> TYPE: DNA
<213> ORGANISM: Artificial Sequence
<220> FEATURE:
<223> OTHER INFORMATION: primer for amplification of Chloramphenichol

<400> SEQUENCE: 5
atggctgaat ggagcggcga atatatcagc ccatacgctg agcacggcaa ggtgtaggct      60
ggagctgctt c                                                          71

<210> SEQ ID NO 6
<211> LENGTH: 65
<212> TYPE: DNA
<213> ORGANISM: Artificial Sequence
<220> FEATURE:
<223> OTHER INFORMATION: primer for amplification of Chloramphenichol

<400> SEQUENCE: 6
gtattcccac gtctccgggt taatccccat ctcacgcatg atctccatat gaatatcctc      60
cttag                                                                 65

<210> SEQ ID NO 7
<211> LENGTH: 19
<212> TYPE: DNA
<213> ORGANISM: Escherichia coli
<220> FEATURE:
<223> OTHER INFORMATION: primer for amplification of metJ

<400> SEQUENCE: 7
gggctttgtc ggtgaaatg                                                  19
```

-continued

```
<210> SEQ ID NO 8
<211> LENGTH: 19
<212> TYPE: DNA
<213> ORGANISM: Escherichia coli
<220> FEATURE:
<223> OTHER INFORMATION: primer for amplification of metJ

<400> SEQUENCE: 8
actttgcgat gagcgagag                                                   19

<210> SEQ ID NO 9
<211> LENGTH: 70
<212> TYPE: DNA
<213> ORGANISM: Escherichia coli
<220> FEATURE:
<223> OTHER INFORMATION: primer for deletion of metA

<400> SEQUENCE: 9

CAATTTCTTG CGTGAAGAAA ACGTCTTTGT GATGACAACT TCTCGTGCGT gtgtaggctg      60

Gagctgcttc                                                             70

<210> SEQ ID NO 10
<211> LENGTH: 70
<212> TYPE: DNA
<213> ORGANISM: Escherichia coli
<220> FEATURE:
<223> OTHER INFORMATION: primer for deletion of metA

<400> SEQUENCE: 10

AATCCAGCGT TGGATTCATG TGCCGTAGAT CGTATGGCGT GATCTGGTAG catatgaata      60

Tcctccttag                                                             70

<210> SEQ ID NO 11
<211> LENGTH: 29
<212> TYPE: DNA
<213> ORGANISM: Deinococcus radiodurans
<220> FEATURE:
<223> OTHER INFORMATION: primer for amplification of metX

<400> SEQUENCE: 11
gggaattcCA Tatgaccgcc gtgctcgcg                                        29

<210> SEQ ID NO 12
<211> LENGTH: 27
<212> TYPE: DNA
<213> ORGANISM: Deinococcus radiodurans
<220> FEATURE:
<223> OTHER INFORMATION: primer for amplification of metX

<400> SEQUENCE: 12

CCCAAGCTTt caactcctga gaaacgc                                          27

<210> SEQ ID NO 13
<211> LENGTH: 24
<212> TYPE: DNA
<213> ORGANISM: Mycobacterium smegmatis
<220> FEATURE:
<223> OTHER INFORMATION: primer for amplification of metX

<400> SEQUENCE: 13

CATATGacga tcatcgaaga acga                                             24

<210> SEQ ID NO 14
<211> LENGTH: 24
```

```
<212> TYPE: DNA
<213> ORGANISM: Mycobacterium smegmatis
<220> FEATURE:
<223> OTHER INFORMATION: primer for amplification of metX

<400> SEQUENCE: 14

AAGCTTtcac cgttgtgcaa gctc                                          24

<210> SEQ ID NO 15
<211> LENGTH: 24
<212> TYPE: DNA
<213> ORGANISM: Pseudomonas aeruginosa
<220> FEATURE:
<223> OTHER INFORMATION: primer for amplification of metX

<400> SEQUENCE: 15

CATATGacga tcatcgaaga acga                                          24

<210> SEQ ID NO 16
<211> LENGTH: 24
<212> TYPE: DNA
<213> ORGANISM: Pseudomonas aeruginosa
<220> FEATURE:
<223> OTHER INFORMATION: primer for amplification of metX

<400> SEQUENCE: 16

AAGCTTtcac cgttgtgcaa gctc                                          24

<210> SEQ ID NO 17
<211> LENGTH: 24
<212> TYPE: DNA
<213> ORGANISM: Escherichia coli
<220> FEATURE:
<223> OTHER INFORMATION: primer for amplification of metA

<400> SEQUENCE: 17
ccggaattcC TACGCCCCCA CATA                                          24

<210> SEQ ID NO 18
<211> LENGTH: 25
<212> TYPE: DNA
<213> ORGANISM: Escherichia coli
<220> FEATURE:
<223> OTHER INFORMATION: primer for amplification of metA

<400> SEQUENCE: 18
cggcggtcat AACCTGATTA CCTCA                                         25

<210> SEQ ID NO 19
<211> LENGTH: 25
<212> TYPE: DNA
<213> ORGANISM: Escherichia coli
<220> FEATURE:
<223> OTHER INFORMATION: primer for amplification of metA

<400> SEQUENCE: 19

Caggagttga TCTTCTGTGA TAGTC                                         25

<210> SEQ ID NO 20
<211> LENGTH: 24
<212> TYPE: DNA
<213> ORGANISM: Escherichia coli
<220> FEATURE:
<223> OTHER INFORMATION: primer for amplification of metA

<400> SEQUENCE: 20
```

```
ccggaattcA CATTGGCGTT GAGC                                    24

<210> SEQ ID NO 21
<211> LENGTH: 25
<212> TYPE: DNA
<213> ORGANISM: Deinococcus radiodurans
<220> FEATURE:
<223> OTHER INFORMATION: primer for amplification of metX

<400> SEQUENCE: 21

TAATCAGGTT atgaccgccg tgctc                                   25

<210> SEQ ID NO 22
<211> LENGTH: 25
<212> TYPE: DNA
<213> ORGANISM: Deinococcus radiodurans
<220> FEATURE:
<223> OTHER INFORMATION: primer for amplification of metX

<400> SEQUENCE: 22

TCACAGAAGA tcaactcctg agaaa                                   25

<210> SEQ ID NO 23
<211> LENGTH: 27
<212> TYPE: DNA
<213> ORGANISM: Escherichia coli
<220> FEATURE:
<223> OTHER INFORMATION: primer for amplification of metA

<400> SEQUENCE: 23
ccggaattcC GCCAGATTCA GCAACGG                                 27

<210> SEQ ID NO 24
<211> LENGTH: 27
<212> TYPE: DNA
<213> ORGANISM: Escherichia coli
<220> FEATURE:
<223> OTHER INFORMATION: primer for amplification of metA

<400> SEQUENCE: 24
ccggaattcC CGCGAATTTT CCAATCA                                 27

<210> SEQ ID NO 25
<211> LENGTH: 32
<212> TYPE: DNA
<213> ORGANISM: Escherichia coli
<220> FEATURE:
<223> OTHER INFORMATION: primer for amplification thrA

<400> SEQUENCE: 25

CTGGCAAAGC TTtcaaagga aaactccttc gt                           32

<210> SEQ ID NO 26
<211> LENGTH: 32
<212> TYPE: DNA
<213> ORGANISM: Escherichia coli
<220> FEATURE:
<223> OTHER INFORMATION: primer for amplification of thrA

<400> SEQUENCE: 26

AGTCGTGATA TCatgcgagt gttgaagttc gg                           32

<210> SEQ ID NO 27
<211> LENGTH: 820
<212> TYPE: PRT
<213> ORGANISM: Escherichia coli
```

```
<220> FEATURE:
<223> OTHER INFORMATION: homoserine dehydrogenase fused with aspartate
      kinase

<400> SEQUENCE: 27
```

| | | | | | | | | | | | | | | |
|---|---|---|---|---|---|---|---|---|---|---|---|---|---|---|
| Met | Arg | Val | Leu | Lys | Phe | Gly | Gly | Thr | Ser | Val | Ala | Asn | Ala | Glu | Arg |
| 1 | | | | 5 | | | | | 10 | | | | | 15 | |

| Phe | Leu | Arg | Val | Ala | Asp | Ile | Leu | Glu | Ser | Asn | Ala | Arg | Gln | Gly | Gln |
|---|---|---|---|---|---|---|---|---|---|---|---|---|---|---|---|
| | | | 20 | | | | | 25 | | | | | 30 | | |

| Val | Ala | Thr | Val | Leu | Ser | Ala | Pro | Ala | Lys | Ile | Thr | Asn | His | Leu | Val |
|---|---|---|---|---|---|---|---|---|---|---|---|---|---|---|---|
| | | | 35 | | | | | 40 | | | | | 45 | | |

| Ala | Met | Ile | Glu | Lys | Thr | Ile | Ser | Gly | Gln | Asp | Ala | Leu | Pro | Asn | Ile |
|---|---|---|---|---|---|---|---|---|---|---|---|---|---|---|---|
| | 50 | | | | | 55 | | | | | 60 | | | | |

| Ser | Asp | Ala | Glu | Arg | Ile | Phe | Ala | Glu | Leu | Leu | Thr | Gly | Leu | Ala | Ala |
|---|---|---|---|---|---|---|---|---|---|---|---|---|---|---|---|
| 65 | | | | | 70 | | | | | 75 | | | | | 80 |

| Ala | Gln | Pro | Gly | Phe | Pro | Leu | Ala | Gln | Leu | Lys | Thr | Phe | Val | Asp | Gln |
|---|---|---|---|---|---|---|---|---|---|---|---|---|---|---|---|
| | | | | 85 | | | | | 90 | | | | | 95 | |

| Glu | Phe | Ala | Gln | Ile | Lys | His | Val | Leu | His | Gly | Ile | Ser | Leu | Leu | Gly |
|---|---|---|---|---|---|---|---|---|---|---|---|---|---|---|---|
| | | | 100 | | | | | 105 | | | | | 110 | | |

| Gln | Cys | Pro | Asp | Ser | Ile | Asn | Ala | Ala | Leu | Ile | Cys | Arg | Gly | Glu | Lys |
|---|---|---|---|---|---|---|---|---|---|---|---|---|---|---|---|
| | | | 115 | | | | | 120 | | | | | 125 | | |

| Met | Ser | Ile | Ala | Ile | Met | Ala | Gly | Val | Leu | Glu | Ala | Arg | Gly | His | Asn |
|---|---|---|---|---|---|---|---|---|---|---|---|---|---|---|---|
| | 130 | | | | | 135 | | | | | 140 | | | | |

| Val | Thr | Val | Ile | Asp | Pro | Val | Glu | Lys | Leu | Leu | Ala | Val | Gly | His | Tyr |
|---|---|---|---|---|---|---|---|---|---|---|---|---|---|---|---|
| 145 | | | | | 150 | | | | | 155 | | | | | 160 |

| Leu | Glu | Ser | Thr | Val | Asp | Ile | Ala | Glu | Ser | Thr | Arg | Arg | Ile | Ala | Ala |
|---|---|---|---|---|---|---|---|---|---|---|---|---|---|---|---|
| | | | | 165 | | | | | 170 | | | | | 175 | |

| Ser | Arg | Ile | Pro | Ala | Asp | His | Met | Val | Leu | Met | Ala | Gly | Phe | Thr | Ala |
|---|---|---|---|---|---|---|---|---|---|---|---|---|---|---|---|
| | | | 180 | | | | | 185 | | | | | 190 | | |

| Gly | Asn | Glu | Lys | Gly | Glu | Leu | Val | Val | Leu | Gly | Arg | Asn | Gly | Ser | Asp |
|---|---|---|---|---|---|---|---|---|---|---|---|---|---|---|---|
| | | | 195 | | | | | 200 | | | | | 205 | | |

| Tyr | Ser | Ala | Ala | Val | Leu | Ala | Ala | Cys | Leu | Arg | Ala | Asp | Cys | Cys | Glu |
|---|---|---|---|---|---|---|---|---|---|---|---|---|---|---|---|
| | 210 | | | | | 215 | | | | | 220 | | | | |

| Ile | Trp | Thr | Asp | Val | Asp | Gly | Val | Tyr | Thr | Cys | Asp | Pro | Arg | Gln | Val |
|---|---|---|---|---|---|---|---|---|---|---|---|---|---|---|---|
| 225 | | | | | 230 | | | | | 235 | | | | | 240 |

| Pro | Asp | Ala | Arg | Leu | Leu | Lys | Ser | Met | Ser | Tyr | Gln | Glu | Ala | Met | Glu |
|---|---|---|---|---|---|---|---|---|---|---|---|---|---|---|---|
| | | | | 245 | | | | | 250 | | | | | 255 | |

| Leu | Ser | Tyr | Phe | Gly | Ala | Lys | Val | Leu | His | Pro | Arg | Thr | Ile | Thr | Pro |
|---|---|---|---|---|---|---|---|---|---|---|---|---|---|---|---|
| | | | 260 | | | | | 265 | | | | | 270 | | |

| Ile | Ala | Gln | Phe | Gln | Ile | Pro | Cys | Leu | Ile | Lys | Asn | Thr | Gly | Asn | Pro |
|---|---|---|---|---|---|---|---|---|---|---|---|---|---|---|---|
| | | | 275 | | | | | 280 | | | | | 285 | | |

| Gln | Ala | Pro | Gly | Thr | Leu | Ile | Gly | Ala | Ser | Arg | Asp | Glu | Asp | Glu | Leu |
|---|---|---|---|---|---|---|---|---|---|---|---|---|---|---|---|
| | 290 | | | | | 295 | | | | | 300 | | | | |

| Pro | Val | Lys | Gly | Ile | Ser | Asn | Leu | Asn | Asn | Met | Ala | Met | Phe | Ser | Val |
|---|---|---|---|---|---|---|---|---|---|---|---|---|---|---|---|
| 305 | | | | | 310 | | | | | 315 | | | | | 320 |

| Ser | Gly | Pro | Gly | Met | Lys | Gly | Met | Val | Gly | Met | Ala | Ala | Arg | Val | Phe |
|---|---|---|---|---|---|---|---|---|---|---|---|---|---|---|---|
| | | | | 325 | | | | | 330 | | | | | 335 | |

| Ala | Ala | Met | Ser | Arg | Ala | Arg | Ile | Phe | Val | Val | Leu | Ile | Thr | Gln | Ser |
|---|---|---|---|---|---|---|---|---|---|---|---|---|---|---|---|
| | | | 340 | | | | | 345 | | | | | 350 | | |

| Ser | Ser | Glu | Tyr | Ser | Ile | Ser | Phe | Cys | Val | Pro | Gln | Ser | Asp | Cys | Val |
|---|---|---|---|---|---|---|---|---|---|---|---|---|---|---|---|
| | | | 355 | | | | | 360 | | | | | 365 | | |

| Arg | Ala | Glu | Arg | Ala | Met | Gln | Glu | Glu | Phe | Tyr | Leu | Glu | Leu | Lys | Glu |
|---|---|---|---|---|---|---|---|---|---|---|---|---|---|---|---|
| | 370 | | | | | 375 | | | | | 380 | | | | |

| Gly | Leu | Leu | Glu | Pro | Leu | Ala | Val | Thr | Glu | Arg | Leu | Ala | Ile | Ile | Ser |
|---|---|---|---|---|---|---|---|---|---|---|---|---|---|---|---|

```
                385                 390                 395                 400
Val Val Gly Asp Gly Met Arg Thr Leu Arg Gly Ile Ser Ala Lys Phe
                    405                 410                 415

Phe Ala Ala Leu Ala Arg Ala Asn Ile Asn Ile Val Ala Ile Ala Gln
                    420                 425                 430

Gly Ser Ser Glu Arg Ser Ile Ser Val Val Asn Asn Asp Asp Ala
                    435                 440                 445

Thr Thr Gly Val Arg Val Thr His Gln Met Leu Phe Asn Thr Asp Gln
                    450                 455                 460

Val Ile Glu Val Phe Val Ile Gly Val Gly Gly Val Gly Gly Ala Leu
465                     470                 475                 480

Leu Glu Gln Leu Lys Arg Gln Gln Ser Trp Leu Lys Asn Lys His Ile
                    485                 490                 495

Asp Leu Arg Val Cys Gly Val Ala Asn Ser Lys Ala Leu Leu Thr Asn
                    500                 505                 510

Val His Gly Leu Asn Leu Glu Asn Trp Gln Glu Glu Leu Ala Gln Ala
                    515                 520                 525

Lys Glu Pro Phe Asn Leu Gly Arg Leu Ile Arg Leu Val Lys Glu Tyr
                    530                 535                 540

His Leu Leu Asn Pro Val Ile Val Asp Cys Thr Ser Ser Gln Ala Val
545                     550                 555                 560

Ala Asp Gln Tyr Ala Asp Phe Leu Arg Glu Gly Phe His Val Val Thr
                    565                 570                 575

Pro Asn Lys Lys Ala Asn Thr Ser Ser Met Asp Tyr Tyr His Gln Leu
                    580                 585                 590

Arg Tyr Ala Ala Glu Lys Ser Arg Arg Lys Phe Leu Tyr Asp Thr Asn
                    595                 600                 605

Val Gly Ala Gly Leu Pro Val Ile Glu Asn Leu Gln Asn Leu Leu Asn
                    610                 615                 620

Ala Gly Asp Glu Leu Met Lys Phe Ser Gly Ile Leu Ser Gly Ser Leu
625                     630                 635                 640

Ser Tyr Ile Phe Gly Lys Leu Asp Glu Gly Met Ser Phe Ser Glu Ala
                    645                 650                 655

Thr Thr Leu Ala Arg Glu Met Gly Tyr Thr Glu Pro Asp Pro Arg Asp
                    660                 665                 670

Asp Leu Ser Gly Met Asp Val Ala Arg Lys Leu Leu Ile Leu Ala Arg
                    675                 680                 685

Glu Thr Gly Arg Glu Leu Glu Leu Ala Asp Ile Glu Ile Glu Pro Val
                    690                 695                 700

Leu Pro Ala Glu Phe Asn Ala Glu Gly Asp Val Ala Ala Phe Met Ala
705                     710                 715                 720

Asn Leu Ser Gln Leu Asp Asp Leu Phe Ala Ala Arg Val Ala Lys Ala
                    725                 730                 735

Arg Asp Glu Gly Lys Val Leu Arg Tyr Val Gly Asn Ile Asp Glu Asp
                    740                 745                 750

Gly Val Cys Arg Val Lys Ile Ala Glu Val Asp Gly Asn Asp Pro Leu
                    755                 760                 765

Phe Lys Val Lys Asn Gly Glu Asn Ala Leu Ala Phe Tyr Ser His Tyr
                    770                 775                 780

Tyr Gln Pro Leu Pro Leu Val Leu Arg Gly Tyr Gly Ala Gly Asn Asp
785                     790                 795                 800

Val Thr Ala Ala Gly Val Phe Ala Asp Leu Leu Arg Thr Leu Ser Trp
                    805                 810                 815
```

Lys Leu Gly Val
        820

<210> SEQ ID NO 28
<211> LENGTH: 23
<212> TYPE: DNA
<213> ORGANISM: Leptospira meyeri
<220> FEATURE:
<223> OTHER INFORMATION: primer for amplification of metX

<400> SEQUENCE: 28

CATATGccta cctccgaaca gaa                                         23

<210> SEQ ID NO 29
<211> LENGTH: 26
<212> TYPE: DNA
<213> ORGANISM: Leptospira meyeri
<220> FEATURE:
<223> OTHER INFORMATION: primer for amplification of metX

<400> SEQUENCE: 29

AAGCTTtcaa aggaaaactc cttcgt                                      26

<210> SEQ ID NO 30
<211> LENGTH: 20
<212> TYPE: DNA
<213> ORGANISM: Corynebacterium glutamicum
<220> FEATURE:
<223> OTHER INFORMATION: primer for amplification of metX

<400> SEQUENCE: 30

CATatgccca ccctcgcgcc                                             20

<210> SEQ ID NO 31
<211> LENGTH: 25
<212> TYPE: DNA
<213> ORGANISM: Corynebacterium glutamicum
<220> FEATURE:
<223> OTHER INFORMATION: primer for amplification of metX

<400> SEQUENCE: 31

AAGCTTttag atgtagaact cgatg                                       25

<210> SEQ ID NO 32
<211> LENGTH: 334
<212> TYPE: PRT
<213> ORGANISM: Deinococcus radiodurans
<220> FEATURE:
<223> OTHER INFORMATION: homoserine O-acetyltransferase peptide
      with Unipro database No. Q9RVZ8

<400> SEQUENCE: 32

Met Thr Ala Val Leu Ala Gly His Ala Ser Ala Leu Leu Leu Thr Glu
1               5                   10                  15

Glu Pro Asp Cys Ser Gly Pro Gln Thr Val Val Leu Phe Arg Arg Glu
            20                  25                  30

Pro Leu Leu Leu Asp Cys Gly Arg Ala Leu Ser Asp Val Arg Val Ala
        35                  40                  45

Phe His Thr Tyr Gly Thr Pro Arg Ala Asp Ala Thr Leu Val Leu His
    50                  55                  60

Ala Leu Thr Gly Asp Ser Ala Val His Glu Trp Trp Pro Asp Phe Leu
65                  70                  75                  80

Gly Ala Gly Arg Pro Leu Asp Pro Ala Asp Asp Tyr Val Val Cys Ala

```
                    85                  90                  95
Asn Val Leu Gly Gly Cys Ala Gly Thr Thr Ser Ala Ala Glu Leu Ala
                100                 105                 110
Ala Thr Cys Ser Gly Pro Val Pro Leu Ser Leu Arg Asp Met Ala Arg
                115                 120                 125
Val Gly Arg Ala Leu Leu Asp Ser Leu Gly Val Arg Val Arg Val
            130                 135                 140
Ile Gly Ala Ser Met Gly Gly Met Leu Ala Tyr Ala Trp Leu Leu Glu
145                 150                 155                 160
Cys Pro Asp Leu Val Glu Lys Ala Val Ile Ile Gly Ala Pro Ala Arg
                165                 170                 175
His Ser Pro Trp Ala Ile Gly Leu Asn Thr Ala Ala Arg Ser Ala Ile
                180                 185                 190
Ala Leu Ala Pro Gly Gly Glu Gly Leu Lys Val Ala Arg Gln Ile Ala
                195                 200                 205
Met Leu Ser Tyr Arg Ser Pro Glu Ser Leu Ser Arg Thr Gln Ala Gly
                210                 215                 220
Gln Arg Val Pro Gly Val Pro Ala Val Thr Ser Tyr Leu His Tyr Gln
225                 230                 235                 240
Gly Glu Lys Leu Ala Ala Arg Phe Asp Glu Gln Thr Tyr Cys Ala Leu
                245                 250                 255
Thr Trp Ala Met Asp Ala Phe Gln Pro Ser Ser Ala Asp Leu Lys Ala
                260                 265                 270
Val Arg Ala Pro Val Leu Val Val Gly Ile Ser Ser Asp Leu Leu Tyr
                275                 280                 285
Pro Ala Ala Glu Val Arg Ala Cys Ala Ala Glu Leu Pro His Ala Asp
                290                 295                 300
Tyr Trp Glu Leu Gly Ser Ile His Gly His Asp Ala Phe Leu Met Asp
305                 310                 315                 320
Pro Gln Asp Leu Pro Glu Arg Val Gly Ala Phe Leu Arg Ser
                325                 330

<210> SEQ ID NO 33
<211> LENGTH: 379
<212> TYPE: PRT
<213> ORGANISM: Pseudomonas aeruginosa
<220> FEATURE:
<223> OTHER INFORMATION: homoserine O-acetyltransferase peptide
      with GenBank Accession No. NP 249081

<400> SEQUENCE: 33

Met Pro Thr Val Phe Pro Asp Asp Ser Val Gly Leu Val Ser Pro Gln
1               5                   10                  15
Thr Leu His Phe Asn Glu Pro Leu Glu Leu Thr Ser Gly Lys Ser Leu
                20                  25                  30
Ala Glu Tyr Asp Leu Val Ile Glu Thr Tyr Gly Glu Leu Asn Ala Thr
            35                  40                  45
Gln Ser Asn Ala Val Leu Ile Cys His Ala Leu Ser Gly His His His
        50                  55                  60
Ala Ala Gly Tyr His Ser Val Asp Glu Arg Lys Pro Gly Trp Trp Asp
65                  70                  75                  80
Ser Cys Ile Gly Pro Gly Lys Pro Ile Asp Thr Arg Lys Phe Phe Val
                85                  90                  95
Val Ala Leu Asn Asn Leu Gly Gly Cys Asn Gly Ser Ser Gly Pro Ala
                100                 105                 110
```

```
Ser Ile Asn Pro Ala Thr Gly Lys Val Tyr Gly Ala Asp Phe Pro Met
            115                 120                 125

Val Thr Val Glu Asp Trp Val His Ser Gln Ala Arg Leu Ala Asp Arg
130                 135                 140

Leu Gly Ile Arg Gln Trp Ala Ala Val Val Gly Gly Ser Leu Gly Gly
145                 150                 155                 160

Met Gln Ala Leu Gln Trp Thr Ile Ser Tyr Pro Glu Arg Val Arg His
                165                 170                 175

Cys Leu Cys Ile Ala Ser Ala Pro Lys Leu Ser Ala Gln Asn Ile Ala
            180                 185                 190

Phe Asn Glu Val Ala Arg Gln Ala Ile Leu Ser Asp Pro Glu Phe Leu
        195                 200                 205

Gly Gly Tyr Phe Gln Glu Gln Gly Val Ile Pro Lys Arg Gly Leu Lys
    210                 215                 220

Leu Ala Arg Met Val Gly His Ile Thr Tyr Leu Ser Asp Asp Ala Met
225                 230                 235                 240

Gly Ala Lys Phe Gly Arg Val Leu Lys Thr Glu Lys Leu Asn Tyr Asp
                245                 250                 255

Leu His Ser Val Glu Phe Gln Val Glu Ser Tyr Leu Arg Tyr Gln Gly
            260                 265                 270

Glu Glu Phe Ser Thr Arg Phe Asp Ala Asn Thr Tyr Leu Leu Met Thr
        275                 280                 285

Lys Ala Leu Asp Tyr Phe Asp Pro Ala Ala Ala His Gly Asp Asp Leu
    290                 295                 300

Val Arg Thr Leu Glu Gly Val Glu Ala Asp Phe Cys Leu Met Ser Phe
305                 310                 315                 320

Thr Thr Asp Trp Arg Phe Ser Pro Ala Arg Ser Arg Glu Ile Val Asp
                325                 330                 335

Ala Leu Ile Ala Ala Lys Lys Asn Val Ser Tyr Leu Glu Ile Asp Ala
            340                 345                 350

Pro Gln Gly His Asp Ala Phe Leu Met Pro Ile Pro Arg Tyr Leu Gln
        355                 360                 365

Ala Phe Ser Gly Tyr Met Asn Arg Ile Ser Val
    370                 375

<210> SEQ ID NO 34
<211> LENGTH: 380
<212> TYPE: PRT
<213> ORGANISM: Mycobacterium smegmatis
<220> FEATURE:
<223> OTHER INFORMATION: homoserine O-acetyltransferase peptide
      with GenBank Accession No.YP 886028

<400> SEQUENCE: 34

Met Thr Ile Ile Glu Glu Arg Ala Thr Asp Thr Gly Met Ala Thr Val
1               5                   10                  15

Pro Leu Pro Ala Glu Gly Glu Ile Gly Leu Val His Ile Gly Ala Leu
            20                  25                  30

Thr Leu Glu Asn Gly Thr Val Leu Pro Asp Val Thr Ile Ala Val Gln
        35                  40                  45

Arg Trp Gly Glu Leu Ala Pro Asp Arg Gly Asn Val Met Val Leu
    50                  55                  60

His Ala Leu Thr Gly Asp Ser His Val Thr Gly Pro Ala Gly Asp Gly
65                  70                  75                  80

His Pro Thr Ala Gly Trp Trp Asp Gly Val Ala Gly Pro Gly Ala Pro
                85                  90                  95
```

-continued

```
Ile Asp Thr Asp His Trp Cys Ala Ile Ala Thr Asn Val Leu Gly Gly
            100                 105                 110

Cys Arg Gly Ser Thr Gly Pro Gly Ser Leu Ala Pro Asp Gly Lys Pro
            115                 120                 125

Trp Gly Ser Arg Phe Pro Gln Ile Thr Ile Arg Asp Gln Val Ala Ala
            130                 135                 140

Asp Arg Ala Ala Leu Ala Ala Leu Gly Ile Thr Glu Val Ala Ala Val
145                 150                 155                 160

Val Gly Gly Ser Met Gly Gly Ala Arg Ala Leu Glu Trp Leu Val Thr
                165                 170                 175

His Pro Asp Asp Val Arg Ala Gly Leu Val Leu Ala Val Gly Ala Arg
            180                 185                 190

Ala Thr Ala Asp Gln Ile Gly Thr Gln Ser Thr Gln Val Ala Ala Ile
            195                 200                 205

Lys Ala Asp Pro Asp Trp Gln Gly Gly Asp Tyr His Gly Thr Gly Arg
            210                 215                 220

Ala Pro Thr Glu Gly Met Glu Ile Ala Arg Arg Phe Ala His Leu Thr
225                 230                 235                 240

Tyr Arg Gly Glu Glu Glu Leu Asp Asp Arg Phe Ala Asn Thr Pro Gln
                245                 250                 255

Asp Asp Glu Asp Pro Leu Thr Gly Gly Arg Tyr Ala Val Gln Ser Tyr
            260                 265                 270

Leu Glu Tyr Gln Gly Gly Lys Leu Ala Arg Arg Phe Asp Pro Gly Thr
            275                 280                 285

Tyr Val Val Leu Ser Asp Ala Leu Ser Ser His Asp Val Gly Arg Gly
            290                 295                 300

Arg Gly Gly Val Glu Ala Ala Leu Arg Ser Cys Pro Val Pro Val Val
305                 310                 315                 320

Val Gly Gly Ile Thr Ser Asp Arg Leu Tyr Pro Ile Arg Leu Gln Gln
                325                 330                 335

Glu Leu Ala Glu Leu Leu Pro Gly Cys Gln Gly Leu Asp Val Val Asp
            340                 345                 350

Ser Ile Tyr Gly His Asp Gly Phe Leu Val Glu Thr Glu Leu Val Gly
            355                 360                 365

Lys Leu Ile Arg Arg Thr Leu Glu Leu Ala Gln Arg
370                 375                 380
```

MICROORGANISM PRODUCING L-METHIONINE PRECURSOR AND THE METHOD OF PRODUCING L-METHIONINE PRECURSOR USING THE MICROORGANISM

BACKGROUND

Methionine is one of essential amino acids of human body which has been widely used as feed and food additives and further used as a synthetic raw material for medical solutions and medical supplies. Methionine acts as a precursor of such compounds as choline (lecithin) and creatine and at the same time is used as a synthetic raw material for cysteine and taurine. Methionine can also provide sulfur. S-adenosyl-methionine is derived from L-methionine and plays a certain role in providing methyl group in human body and also is involved in the synthesis of various neurotransmitters in the brain. Methionine and/or S-adenosyl-L-methionine (SAM) inhibits fat accumulation in the liver and artery and alleviates depression, inflammation, liver disease, and muscle pain, etc.

The in vivo functions of methionine and/or S-adenosyl-L-methionine known so far are as follows.

1) It inhibits fat accumulation in the liver and artery promoting lipid metabolism and improves blood circulation in the brain, heart and kidney (J Hepatol. Jeon B R et al., March 2001; 34(3): 395-401).

2) It promotes digestion, detoxication and excretion of toxic substances and excretion of heavy metals such as Pb.

3) It can be administered as an anti-depression agent at the dosage of 800-1,600 mg/day (Am J Clin Nutr. Mischoulon D. et al., November 2002; 76(5): 1158S-61S).

4) It enhances liver functions (FASEB J. Mato J M., January 2002; 16(1): 15-26) and particularly is effective in the liver disease caused by alcohol (Cochrane Database Syst Rev., Rambaldi A., 2001; (4): CD002235).

5) It has anti-inflammatory effect on bone and joint diseases and promotes joint-recovery (ACP J Club. Sander O., January-February 2003; 138(1): 21, J Fam Pract., Soeken K L et al., May 2002; 51 (5): 425-30).

6) It is an essential nutrient for hair. It provides nutrition to hair and thereby prevents hair loss (Audiol Neurootol., Lockwood D S et al., September-October 2000; 5(5): 263-266).

Methionine can be chemically or biologically synthesized to be applied to feed, food and medicines.

In the chemical synthesis, methionine is mostly produced by hydrolysis of 5-(β-methylmercaptoethyl)-hydantoin. The chemically synthesized methionine has a disadvantage of only being produced as a mixed form of L-type and D-type.

In the biological synthesis, methionine is produced by method the using proteins involved in methionine synthesis. L-methionine is biosynthesized from homoserine by the action of the enzyme expressed by such genes as metA, metB, metC, metE, and metH, in *E. coli*. Particularly, metA is the gene encoding homoserine O-succinyltransferase which is the first enzyme necessary for methionine biosynthesis, and it converts homoserine into O-succinyl-L-homoserine. O-succinylhomoserine lyase or cystathionine gamma synthase encoded by metB gene converts O-succinyl-L-homoserine into cystathionine. Cystathionine beta lyase encoded by metC gene converts cystathionine into L-homocysteine. MetE encodes cobalamine-independent methionine synthase and metH encodes cobalamine-dependent methionine synthase, both of which convert L-homocysteine into L-methionine. At this time, 5,10-methylenetetrahydrofolate reductase encoded by metF and serine hydroxymethytransferase encoded by glyA work together to synthesize N(5)-methyltetrahydrofolate providing methyl group necessary for L-methionine synthesis.

L-methionine is synthesized by a series of organic reactions by the above enzymes. The genetic modification on the above proteins or other proteins affecting the above proteins might result in the increase of L-methionine synthesis. For example. Japanese Laid-Open Patent Publication No. 2000/139471 describes a method of producing L-methionine with the *Escherichia* sp. of which thrBC and metJ genes on the genome are deleted, metBL is over-expressed and metK is replaced by a leaky mutant. Also, US Patent Publication No. US2003/0092026 A1 describes a method using a metD (L-methionine synthesis inhibitor) knock-out microorganism which belongs to *Corynebacterium* sp. US Patent Publication No. US2002/0049305 describes a method to increase L-methionine production by increasing the expression of 5,10-methylenetetrahydrofolate reductase (metF).

The methionine produced by the biological method is L-type, which has advantages but the production amount is too small. This is because the methionine biosynthetic pathway has very tight feed-back regulation systems. Once methionine is synthesized to a certain level, the final product methionine inhibits the transcription of metA gene encoding the primary protein for initiation of methionine biosynthesis. Over-expression of metA gene itself cannot increase methionine production because the metA gene is suppressed by methionine in the transcription stage and then degraded by the intracellular proteases in the translation stage (Dvora Biran. Eyal Gur, Leora Gollan and Eliora Z. Ron: Control of methionine biosynthesis in *Escherichia coli* by proteolysis: Molecular Microbiology (2000) 37(6), 1436-1443). Therefore, many of previous patents were focused on how to free the metA gene from its feed-back regulation system (WO2005/108561, WO1403813).

US patent publication No. US2005/0054060A1 describes a method to synthesize homocysteine or methionine by modified cystathionine synthase (O-succinylhomoserine lyase) which use methylmercaptan ($CH_3SH$) or hydrogen sulfide ($H_2S$) directly as a sulfur source, not cysteine. However, it is well understood by those in the art that cystathionine synthase can bind various methionine precursor in the cells and thereby produce by-product at high level. For example, it was reported that cystathionine synthase accumulate high levels of homolanthionin by side reaction of O-succinylhomoserine and homocysteine (J. Bacteriol (2006) vol 188:p 609-618). Therefore, overexpression of cystathionine synthase can reduce the efficiency of Intracellular reaction due to the increase of their side reaction. In addition, this method has many disadvantages. This process uses intracellular metabolic pathways which have side reactions and feed back regulation systems. Also this process uses $H_2S$ or $CH_3SH$ which has a severe cytoloxity to cells. Hence the methionine production yield is comparatively small.

To solve these problems, the present inventor had developed two step process comprising; first step of producing of L-methionine precursor by *E. coli* fermentation; and second step of converting L-methionine precursor into L-methionine by enzyme reaction (PCT/KR2007/003650), the contents of which are incorporated herein by reference. This two step process can solve the above problems, such as cytotoxicity of sulfides, feed-back regulation by methionine and SAMe, decomposition of intermediate product by intracellular enzymes (e.g. cystathionine gamma synthase, O-succinylhomoserine sulfhydrylase and O-acetylhomoserine sulfhydrylase). Moreover, against the chemical methionine synthetic method which produce mixed form of D-methionine and L-methionine, the two step process is very efficient to produce only L-methionine selectively.

In this two step process, production yield of methionine precursor is one of the key factor for the increase of methionine production yield. To increase the synthetic yield of methionine precursor, O-acetyl homoserine, good combination of strong aspartokinase, homoserine transferase and O-acetyl homoserine transferase is really important. On the above-mentioned background, the present inventors were constructed the L-methionine precursor producing strain which is characterized by the followings; a) the homoserine O-acetyltransferase activity (EC2.3.1.31) is introduced and enhanced by the integration of genes selected among from *Corynebacterium* sp., *Leptospira* sp., *Deinococcus* sp., *Pseudomonas* sp., and *Mycobacterium* sp.;

b) the aspartokinase or homoserine dehydrogenase activity (EC2.7.2.4 or 1.1.1.3) is enhanced, or c) a combination of a) and b).

BRIEF SUMMARY OF THE INVENTION

The present invention provides a microorganism producing L-methionine precursor and a method of producing L-methionine precursor using the microorganism.

More particularly, the present invention provides a L-methionine precursor producing strain which is characterized by the followings;

a) the homoserine O-acetyltransferase activity (EC2.3.1.31) is introduced and enhanced by the integration of genes selected from *corynebacterium* sp., *Leptospira* sp., *Deinococcus* sp., *Pseudomonas* sp., or *Mycobacterium* sp.;

b) the aspartokinase or homoserine dehydrogenase activity (EC2.7.2.4 or 1.1.1.3) is enhanced, or c) a combination of a) and b), and a method of producing L-methionine precursor using the strain.

BRIEF DESCRIPTION OF THE DRAWINGS

The application of the preferred embodiments of the present invention is best understood with reference to the accompanying drawings, wherein.

DETAILED DESCRIPTION

Figure 1:
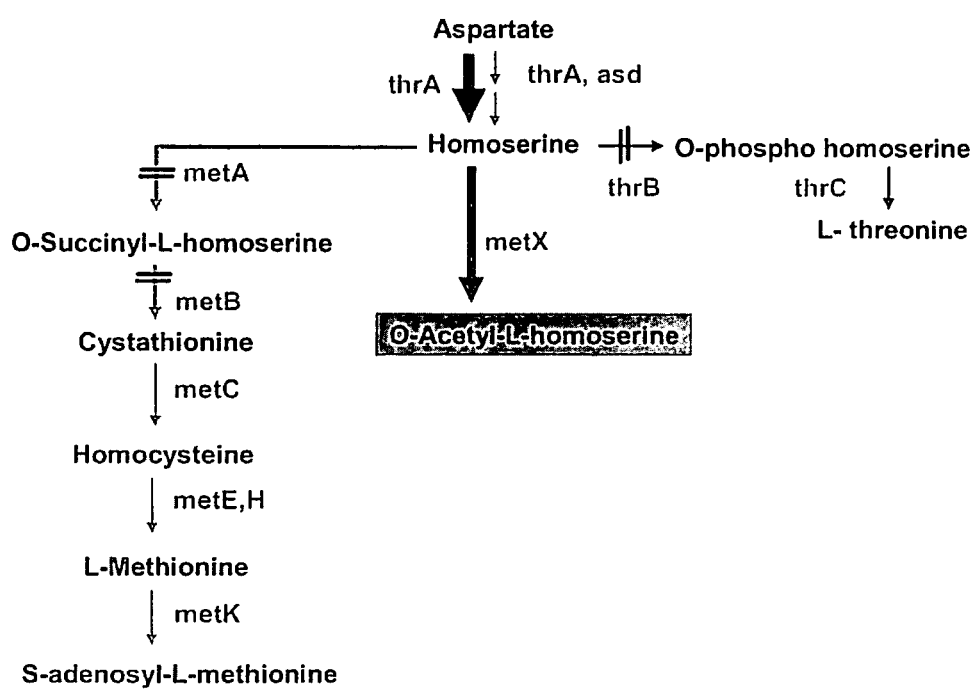
FIG. 1 is a diagram illustrating genetic manipulation of the methionine precursor producing strain.
Figure 2:
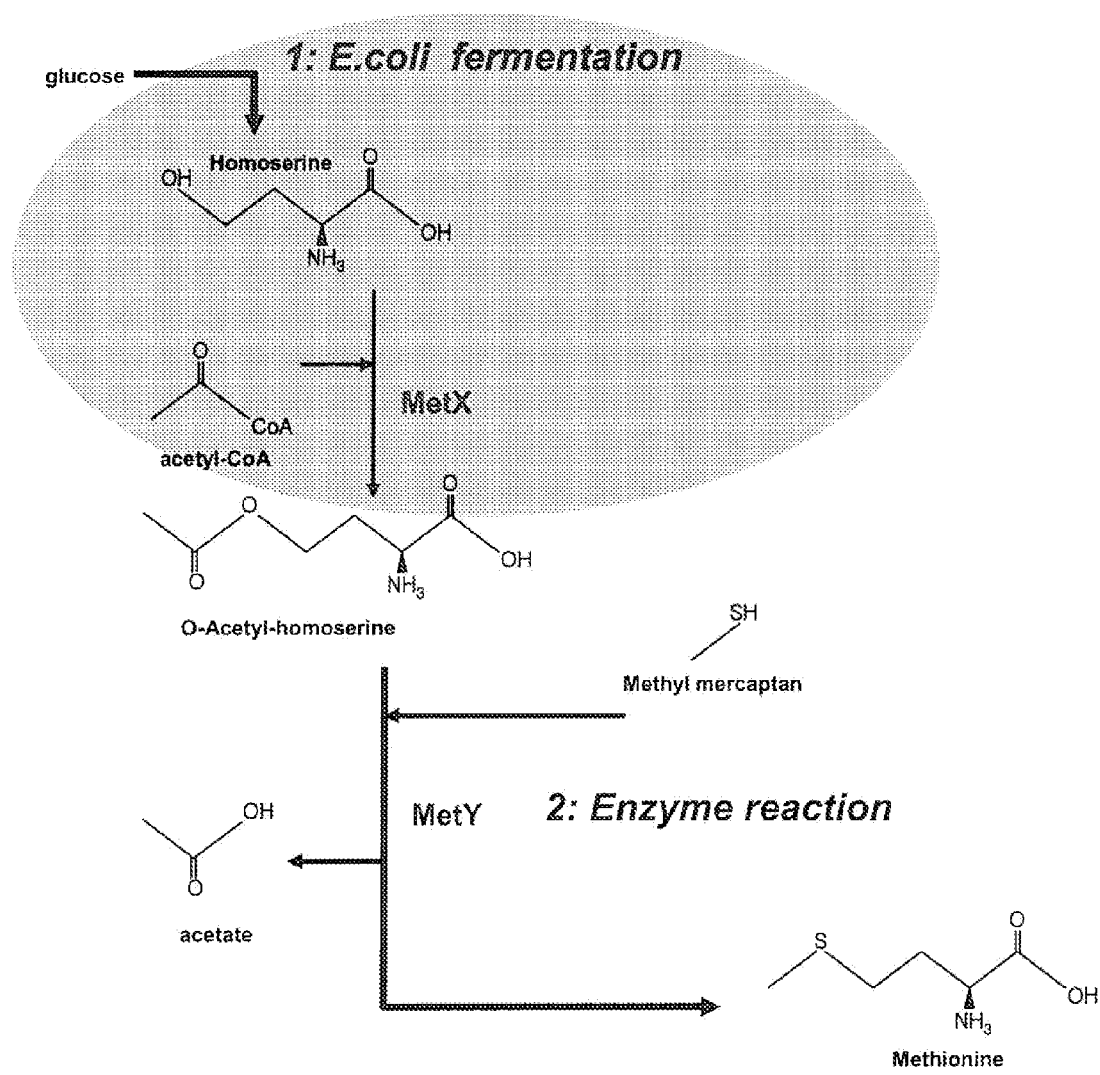
FIG. 2 is a diagram illustrating chemical structures of 2 step process for the production of methionine.
Figure 3:
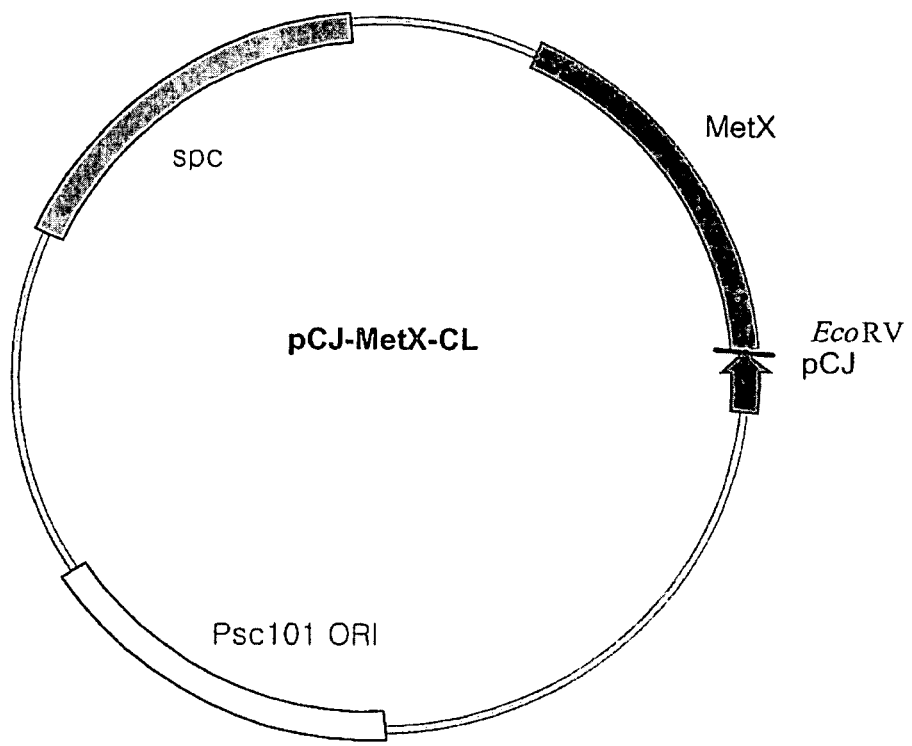
FIG. 3 is a schematic diagram of pCJ-MetX-CL for the expression of metX gene.

The present invention provides microorganisms producing O-acetylhomoserine. In one aspect of the invention, the microorganisms are prokaryotes or eukaryotes containing an exogenous recombinant gene or a vector encoding homoserine O-acetyltransferase, a derivative or active fragment thereof, or a subunit of homoserine O-acetyltransferase. The derivative or active fragment of homoserine O-acetyltransferase or a subunit of homoserine O-acetyltransferase maintaining the activity of the enzyme is contemplated within the scope of the present invention. More particularity, the gene encoding homoserine O-acetyltransferase or a fragment thereof includes genes from among *Corynebacterium* sp., *Leptospira* sp., *Deinococcus* sp., *Pseudomonas* sp., or *Mycobacterium* sp.

In other aspect of the invention, a microorganism is a prokaryotic or a eukaryotic microorganism containing the aspartokinase or homoserine dehydrogenase activity (EC2.7.2.4 or 1.1.1.3) which is enhanced compared to the wild type microorganism.

In one preferred aspect, the recombinant cells are *Escherichia* sp., preferably.

In accordance with an aspect thereof, the present invention is directed to a L-methionine precursor-producing strain characterized by the followings; a) the homoserine O-acetyltransferase activity (EC2.3.1.31) is introduced and enhanced by the integration of genes selected from *Corynebacterium* sp., *Leptospira* sp., *Deinococcus* sp., *Pseudomonas* sp., *Mycobacterium* sp. and a combination thereof;

b) the aspartokinase or homoserine dehydrogenase activity (EC2.7.2.4 or 1.1.1.3) is enhanced, or c) a combination of a) and b).

In another aspect of the present invention, there are provided methods of producing L-methionine precursor using the microorganisms described herein The term "L-methionine precursor" is defined as metabolites that are part of the methionine specific metabolic pathway or can be derived of these metabolites. Particular, L-methionine precursor as used herein refers to a O-acetylhomoserine.

The term "L-methionine precursor-producing strain" or "recombinant cell", as used herein refers to a prokaryotic or eukaryotic microorganism strain that is able to accumulate L-methionine precursor by manipulation according to the present invention. For example, the strain includes *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp. and *Norcardia* sp. microorganisms or fungi or yeasts. Preferably, the microorganisms of *Escherichia* sp., *Corynebacterium* sp., *Leptospira* sp. and yeasts can be used to produce O-acetylhomoserine. More preferably, the microorganisms of *Escherichia* sp. can be used, and most preferably *Escherichia coli* (hereinafter referred to as "*E. coli*") can be used.

In one aspect of the invention, the present invention provides an L-methionine precursor-producing strain in which a gene involved in the decomposition or degradation of authentic O-succinyl homoserine or O-acetylhomoserine is deleted or weakened and instead a gene involved in the synthesis of O-acetylhomoserine is introduced or enhanced. The present invention also selectively provides a strain in which threonine biosynthesis pathway is suppressed, blocked, inhibited or weakened to enhance O-acetylhomoserine production. The present invention further provides a strain in which homoserine O-acetyltransferase free from a feedback regulation system (negative feedback) is introduced, over-expressed or activity-enhanced. The present invention further provides a strain in which aspartokinase or homoserine dehydrogenase is over-expressed or activity-enhanced. The present invention also provides a strain in which homoserine O-acetyltransferase free from feed back regulation system is introduced, over-expressed or activity-enhanced and aspartokinase or homoserine dehydrogenase is over-expressed or activity-enhanced.

In one preferred aspect, the present invention provides an L-methionine precursor producing strain by deleting metB gene involved in the decomposition of L-methionine precursor, thrB gene involved in threonine biosynthesis pathway and metJ gene regulating the transcription of L-methionine precursor production genes. The present invention also provides an L-methionine precursor producing strain by knocking-out authentic metA or metX gene involved in the synthesis of methionine precursor and by introducing foreign metX.

The present invention also provides an L-methionine precursor producing strain by enhancing the activity encoded by the thrA gene.

More preferably, the present invention also provides an L-methionine precursor producing strain by knocking-out authentic or endogenous metA or metX gene involved in the synthesis of methionine precursor and by introducing foreign or exogenous metX gene free from feed-back system and by enhancing the activity encoded by the thrA gene.

In the present invention, "inactivation, inhibition or suppression" as used herein refers to a deletion or an attenuation of the gene. A deletion of the gene is performed by cutting out of a region of the gene or modifying the protein sequence by introducing a specific gene sequence on the chromosome. The term "attenuation", "suppressing" or "weakening" in this connection describes the reduction or elimination of the intracellular activity of one or more enzymes (proteins) in a microorganism which are encoded by the corresponding DNA, for example by reducing the activity of the protein by modifying a promoter region of the gene and the nucleotide sequence of 5'-UTR or by introducing the mutation in the ORF region of the target gene.

To achieve an attenuation, for example, expression of the gene or the catalytic properties of the enzyme proteins can be reduced or eliminated. The two measures can optionally be combined.

The reduction in gene expression can take place, for example, by suitable culturing, by genetic modification (mutation) of the signal structures of gene expression or also by antisense-RNA technique known in the art without undue experimentation. Signal structures of gene expression are, for example, repressor genes, activator genes, operators, promoters, attenuators, ribosome binding sites, the start codon and terminators. The expert can find information in this respect, inter alia, for example, in Jensen and Hammer (Biotechnology and Bioengineering 58: 191 195 (1998)), in Carrier and Keasling (Biotechnology Progress 15: 58 64 (1999)), Franch and Gerdes (Current Opinion in Microbiology 3: 159 164 (2000)) and in known textbooks of genetics and molecular biology, such as, for example, the textbook of Knippers ("Molecular Genetics", 6th edition, 1995) or that of Winnacker ("Genes and Clones", 1990), the contents of each of which are incorporated herein by reference.

Mutations which lead to a change or reduction in the catalytic properties of enzyme proteins are known from the prior art. Examples which may be mentioned are the works of Qiu and Goodman (Journal of Biological Chemistry 272: 8611 8617 (1997)), Yano et al. (Proceedings of the National Academy of Sciences, USA 95: 5511 5515 (1998)), and Wente and Schachmann (Journal of Biological Chemistry 266: 20833 20839 (1991)). Summarizing descriptions can be found in known textbooks of genetics and molecular biology, such as e.g. that by Hagemann ("General Genetics", 1986), the contents of each of which are incorporated herein by reference.

Possible mutations are transitions, transversions, insertions and deletions. Depending on the effect of the amino acid exchange on the enzyme activity, "missense mutations" or nonsense mutations are referred to. Insertions or deletions of at least one base pair in a gene lead to "frame shift mutations", which lead to incorrect amino acids being incorporated or translation being interrupted prematurely. If a stop codon is formed in the coding region as a consequence of the mutation, this also leads to a premature termination of the translation. Deletions of several codons typically lead to a complete loss of the enzyme activity. Instructions on generation of such mutations are prior art and can be found in known textbooks of genetics and molecular biology, such as e.g. the textbook by Knippers ("Molecular Genetics", 6th edition, 1995), that by Winnacker ("Genes and Clones", 1990) or that by Hagemann ("General Genetics", 1986), the contents of each of which are incorporated by reference. Suitable mutations in the genes, such as, for example, deletion mutations, can be incorporated into suitable strains by gene or allele replacement.

In the present invention, the term "enhancement" describes the increase in the intracellular activity of an enzyme which is encoded by the corresponding DNA. The enhancement of intracellular activity of an enzyme can be achieved by the overexpression of the gene. Overexpression of the target gene can be achieved by modifying the promoter region of the gene or the nucleotide sequence of the 5'-UTR region. Overexpression of the target gene can also be achieved by introducing the extra copy of the target gene on the chromosome, by transforming the host strain with the vector containing the target gene with a promoter, or by introducing the mutation which can increase the expression in the target gene. The enhancement of the intracellular activity of an enzyme can also be achieved by introducing the mutation in the ORF region of the target gene. By enhancement measures, the activity or concentration of the corresponding protein is in general increased by at least about 10%, preferably i.e. at least about 25%, 50%, 75%, 100%, 150%, 200%, 300%, 400% or 500%, up to a maximum of 1000% or 2000%, based on that of the wild-type protein or the activity or concentration of the protein in the starting microorganism.

In a preferred embodiment of the present invention, the method for preparing an L-methionine precursor producing strain is as follows:

In step 1, a gene encoding such proteins as cystathionine gamma synthase, O-succinylhomoserine sulfhydrylase or O-acetylhomoserine sulfhydrylase is deleted or weakened in a strain in order to accumulate L-methionine precursor such as O-succinyl homoserine or O-acetyl homoserine.

The gene encoding cystathionine gamma synthase is indicated as metB, the gene encoding O-succinylhomoserine sulfhydrylase is indicated as metZ, and the gene encoding O-acetylhomoserine sulfhydrylase is indicated as metY. A gene encoding the protein having the above mentioned activity is exemplified by metB in *Escherichia coli*. The genomic sequence of the gene can be obtained from the genomic sequence of *E. coli* (Accession no. AAC75876) informed in the previous report (Blattner et. al., Science 277: 1453-1462 (1997)). The above genomic sequence also can be obtained from NCBI (National Center for Biotechnology Information) and DDBJ (DNA Data Bank Japan). Other genes having the same activity are exemplified by metB and metY derived from *Corynebacterium*, and metZ derived from *Pseudomonas*.

Cystathionine gamma synthase, O-succinylhomoserine sulfhydrylase or O-acetylhomoserine sulfhydrylase has the activity to convert O-succinyl homoserine or O-acetylhomoserine into cystathionine or homocysteine as shown in the following reaction formulas. Therefore, where a gene having this activity is deleted or weakened, O-succinylhomoserine or O-acetylhomoserine is excessively accumulated in the culture solution.

L-cysteine+O-succinyl-L-homoserine<=>succinate+cystathionine

L-cysteine+O-acetyl-L-homoserine<=>acetate+cystathionine

HS⁻+O-succinyl-L-homoserine<=>succinate+homocysteine

HS⁻+O-acetyl-L-homoserine<=>acetate+homocysteine

In step 2, thrB gene of encoding homoserine kinase in the strain prepared in step 1 is deleted or weakened. The thrB gene is involved in the synthesis of O-phosphohomoserine from homoserine, which is then converted into threonine by thrC gene. The thrB gene is deleted or weakened in order to use all the produced homoserine for the synthesis of methionine precursor.

In step 3, a transcription regulator of methionine synthetic pathway is deleted or weakened. The metA, metB, metC, metE, and metF gene involved in the methionine synthesis is repressed by feed-back regulation system. The metJ gene is a typical transcriptor regulator gene in *E. coli*. To let the metA or metX gene be over-expressed to synthesize methionine precursor, metJ needs to be eliminated. Therefore, metJ gene is eliminated in *E. coli*, the metA or metX gene expression is always increased, leading to the mass-production of L-methionine precursor.

The above steps 2 and 3 can be modified or eliminated according to a precursor producing strain. However, it can be more preferably executed to enhance the precursor production pathway in the microorganism of *Escherichia* sp.

In step 4, metX gene encoding homoserine O-acetyltransferase which mediate the first process of methionine biosynthesis pathway is introduced in order to increase synthesis of O-acetylhomoserine, L-methionine precursor. The metX is a common designation of gene encoding the protein having activity of homoserine O-acetyltransferase, and a novel foreign homoserine O-acetyltransferase can be obtained from various microorganism species. For example, the homoserine O-acetyltransferase peptide is encoded by the genes from the *corynebacterium* sp., *Leptospira* sp., *Deinococcus* sp., *Pseudomonas* sp., or *Mycobacterium* sp. Preferably, homoserine O-acetyltransferase peptide is encoded by the genes derived from *Corynebacterium glutamicum*, *Leptospira meyeri*, *Deinococcus radiodurans*, *Pseudomonas aeruginosa*, or *Mycobacterium smegmatis*. More preferably, the homoserine O-acetyltransferase peptide has amino acid sequence of Unipro database No. Q9RVZ8 (*Deinococcus radiodurans*, SEQ. ID. NO: 32), or GenBank Accession No. NP 249081 (*Pseudomonas aeruginosa*, SEQ. ID. NO: 33) or YP_886028 (*Mycobacterium smegmatis*, SEQ. ID. NO: 34). The metX gene from *leptospira meyeri* was known as feed back resistant to methionine (J Bacteriol. January 1998; 180 (2):250-5. Belfaiza J et al.), incorporated herein by reference and several homoserine O-acetyltransferase were confirmed as feed back resistant in our lab before.

The introduction and enhancement of the metX gene expression can be performed by the introduction of the gene or by the modification of a promoter region of the gene and the nucleotide sequence of 5'-UTR or by introducing the mutation in the ORF region of the target gene. The enhancement of metX gene expression results in the increase of methionine precursor synthesis.

In step 5, aspartokinase or homoserine dehydrogenase is activity-enhanced in order to increase synthesis of homoserine which is the precursor of O-succinyl homoserine or O-acetyl homoserine. The thrA is a common designation of gene encoding the peptide having activity of aspartokinase and homoserine dehydrogenase. Preferably, an aspartokinase and homoserine dehydrogenase encoded by the gene from Unipro database No: AP_000666. More preferably, the amino acid sequence encoded by the thrA gene is represented in SEQ. ID. NO: 27 that has mutation at amino acid position 345, the contents of which are incorporated herein by reference. Enhancement of the thrA activity is performed by introducing the mutation in the thrA gene or by further introducing the target gene on the chromosome or by further introducing processed plasmid.

O-acetylhomoserine which is L-methionine precursor, can be accumulated in a strain by taking advantage of a part or the entire process of the above step 1 to step 5.

The L-methionine precursor-producing strain can be prepared from the strain producing L-lysine, L-threonine or L-isoleucine, or a combination thereof. Preferably, it can be prepared by using the L-threonine producing strain. With this strain, homoserine synthesis is going easier and the production of methionine precursor is resultantly increased. So, methionine precursor can be accumulated by deleting or weakening a gene involved in threonine biosynthesis pathway and then metA or metY or metZ gene, using the L-threonine producing strain. It is more preferred to delete or weaken thrB gene first and then metB, met Y or metZ to synthesize methionine precursor. In the meantime, the enhancement of metX gene expression results in the increase of methionine precursor synthesis.

The term, "L-threonine-producing strain" of the invention refers to a prokaryotic or eukaryotic microorganism strain that is able to produce L-threonine in vivo. For example, the strain can be include L-threonine producing microorganism strains belongs to *Escherichia* sp., *Erwinia* sp., *Serratia* sp., *Providencia* sp., *Corynebacterium* sp. and *Brevibacterium* sp. Among these, *Escherichia* sp. microorganism is preferred and *Escherichia coli* is more preferred.

In a preferred embodiment of the present invention, CJM002, the L-threonine producing and L-methionine-independent strain transformed from TF4076 (KFCC 10718, Korean Patent No. 92-8365, incorporated herein by reference), the L-threonine producing *E. coli* mutant strain, was used. TF4076 has a requirement for methionine, and is resistant to methionine analogues (ex, a-amino-β-hydroxy valeric acid, AHV), lysine analogues (ex, S-(2-aminoethyl)-L-cysteine, AEC), and isoleucine analogues (ex, a-aminobutylic acid). The TF4076 is not able to synthesize methionine in vivo because it is the strain which has a requirement for methionine. To use this strain as the methionine precursor producing strain of the invention by free from a requirement for methionine, the present inventors prepared the L-threonine producing strain *E. coli* CJM002 free from the requirement for methionine by artificial mutation using NTG. The *E. coli* CJM002 was named as *Escherichia coli* MF001 and deposited at KCCM (Korean Culture Center of Microorganism, Eulim Buld., Hongie-l-Dong, Seodaemun-Ku, Seoul, 361-221, Korea) on Apr. 9, 2004 (Accession No: KCCM-10568). In the present invention, the metB, thrB, metJ and metA gene of the *E. coli* CJM002 were deleted, then the metX gene was introduced in the metA locus. The resulting L-methionine precursor producing strain constructed using *E. coli* CJM002 was named CJM-X. The metX gene of CJM-X strain derived from *D. radiodurans*. The *Escherichia coli* CJM-X, O-acetylhomoserine producing strain, prepared by the above method was deposited on Jan. 23, 2008, with the accession No. KCCM 10921P.

The CJM-X strain was transformed with the thrA expression vector, and was named CJM-X (pthrA(M)-CL).

In another preferred embodiment of the present invention, FTR2533 which is the L-threonine producing strain disclosed in PCT/KR2005/00344. incorporated herein by reference, was used. FTR2533 was derived from *Escherichia coli* TFR7624 which was derived from *Escherichia coli* Accession No. KCCM10236. And *Escherichia coli* Accession No. KCCM 10236 which was derived from *Escherichia coli* TF4076. *Escherichia coli* Accession No. KCCM 10236 is, capable of expressing higher levels of the ppc genes catalyzing the formation oxaloacetate from PEP and the enzymes necessary for threonine biosynthesis from aspartate e.g. thrA: aspartokinase 1-homoserine dehydrogenase, thrB: homoserine kinase, thrC: threonine synthase, thereby enabling an increase in L-threonine production. And *Escherichia coli* FTR7624 (KCCM10538) have an inactivated tyrR gene which regresses the expression of tyrB gene necessary for L-threonine biosynthesis. And *Escherichia coli* FTR2533 (KCCM10541) is the L-threonine producing strain having an in-activated galR gene, the L-threonine producing *E. coli* mutant strain.

In the present invention, the metB, thrB, metJ and metA gene of the *E. coli* FTR2533 were deleted, then the metX gene was introduced in the metA locus. The result L-methionine precursor producing strain constructed using *E. coli* FTR2533 was named CJM2-X. The metX gene of CJM2-X strain derived from *D. radiodurans*. The *Escherichia coli* CJM2-X was deposited on Feb. 12, 2008, with the accession No. KCCM 10925P.

The CJM2-X strain was transformed with the thrA expression vector, and was named CJM2-X (pthrA(M)-CL).

In another aspect, the present invention provides a method of producing L-methionine precursor. The method includes: a) fermentation of the above microorganisms described herein and b) enrichment of the L-methionine precursor in the medium or in the microorganisms. Alternatively, the method includes: a) culturing the recombinant cell described herein and isolating O-acetylhomoserine. Any standard methods of culture and isolation known in the art can be contemplated within the scope of the present invention.

The culture of the L-methionine precursor producing strain prepared above can be performed by a proper medium and conditions known to those in the art. It is well understood by those in the art that the culture method can be used by easily adjusting, according to the selected strain. For example, the culture method includes, but not limited to batch, continuous culture and fed-batch. A variety of culture methods are described in the following reference: "Biochemical Engineering" by James M. Lee, Prentice-Hall International Editions, pp 138-176.

The medium has to meet the culture conditions for a specific strain. A variety of microorganism culture mediums are described in the following reference: "Manual of Methods for General Bacteriology" by the American Society for Bacteriology, Washington D.C., USA, 1981. Those mediums include various carbon sources, nitrogen sources and trace elements. The carbon source is exemplified by carbohydrate such as glucose, sucrose, lactose, fructose, maltose, starch, cellulose; fat such as soybean oil, sunflower oil, castor oil and coconut oil; fatty acid such as palmitic acid, stearic acid, and linoleic acid; alcohol such as glycerol and ethanol; and organic acid such as acetic acid. One of these compounds or a mixture thereof can be used as a carbon source. The nitrogen source is exemplified by such organic nitrogen source as peptone, yeast extract, gravy, malt extract, corn steep liquor (CSL) and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source. The medium herein can additionally include potassium dihydrogen phosphate, dipotassium hydrogen phosphate and corresponding sodium-containing salts as a phosphate source. The medium also can include a metal salt such as magnesium sulfate or iron sulfate. In addition, amino acids, vitamins and proper precursors can be added as well. The mediums or the precursors can be added to the culture by batch-type or continuous type.

PH of the culture can be adjusted during the cultivation by adding in the proper way such a compound as ammonium hydroxide, potassium hydroxide, ammonia, phosphoric acid and sulfuric acid. The generation of air bubbles can be inhibited during the cultivation by using an antifoaming agent such as fatty acid polyglycol ester. To maintain aerobic condition of the culture, oxygen or oxygen-containing gas (ex, air) can be injected into the culture. The temperature of the culture is conventionally 20-45° C., preferably 25-40° C. The period of cultivation can be continued until the production of L-methionine precursor reaches a wanted level, and the preferable cultivation time is 10-160 hours.

EXAMPLES

Practical and presently preferred embodiments of the present invention are illustrative as shown in the following Examples which are set forth to illustrate, but are not to be construed as the limit of the present invention. It will be appreciated that those skilled in the art, on consideration of this disclosure, may make modifications and improvements within the spirit and scope of the present invention.

Example 1

Construction of a Methionine Precursor Producing Strain

<1-1> Deletion of MetB Gene

To delete the metB gene encoding cystathionine synthase in *E. coli* strain, FRT-one-step PCR deletion was performed (PNAS (2000) vol 97: P 6640-6645). Primers of SEQ. ID. NO: 1 and NO: 2 were used for PCR using pKD3 vector (PNAS (2000) vol 97: P 6640-6645) as a template, resulting in the construction of deletion cassette. PCR was performed as follows; 30 cycles of denaturation at 94° C. for 30 seconds, annealing at 55° C. for 30 seconds, extension at 72° C. for 1 minute.

The PCR product was electrophoresised on 1.0% agarose gel, followed by purification of DNA obtained from 1.2 kbp band. The recovered DNA fragment was electroporated into *E. coli* (K12) W3110 transformed with pKD46 vector (PNAS (2000) vol 97: P 6640-6645). Before electroporation, W3110 transformed with pKD46 was cultivated at 30° C. in LB medium containing 100 μg/L of ampicillin and 5 mM of L-arabinose until $OD_{600}$ reached 0.6. Then, the cultured strain was washed twice with sterilized distilled water and one more time with 10% glycerol. Electroporation was performed at 2500 V. The recovered strain was streaked on LB plate medium containing 25 μg/L of chloramphenicol, followed by culture at 37° C. for overnight. Then, a strain exhibiting resistance to chloramphenicol was selected.

PCR was performed by using the selected strain as a template with the primers No 1 and 2 under the same condition. The deletion of metB gene was identified by confirming the 1.2 kb sized gene on 1.0% agarose gel. The strain was then transformed with pCP20 vector (PNAS (2000) vol 97: P 6640-6645) and cultured in LB medium to eliminate the chloramphenichol marker gene. The final metB knock-out strain was constructed in which the size of metB gene reduced to 150 bp on 1.0% agarose gel by PCR under the same conditions. The constructed strain was named W3-B.

<1-2> Deletion of ThrB Gene

The inventors tried to increase O-acetylhomoserine synthesis from homoserine by deletion of thrB gene encoding homoserine kinase. Particularly, when the threonine producing strain is used as a production host of O-acetylhomoserine, deletion of thrB gene is necessary because conversion of homoserine to O-phosphohomoserine by this gene is very strong. To delete thrB gene in the W3-B strain constructed above, FRT one step PCR deletion was performed by the same manner as described above for the deletion of metB gene.

To construct thrB deletion cassette, PCR was performed by using pKD4 vector (PNAS (2000) vol 97: P 6640-6645) as a template with primers of SEQ. ID. NO: 3 and NO: 4 as follows; 30 cycles of denaturation at 94° C. for 30 seconds, annealing at 55° C. for 30 seconds, extension at 72° C. for 1 minute. The PCR product was electrophoresed on 1.0% agarose gel. followed by purification of DNA obtained from 1.6 kbp band. The recovered DNA fragment was electroporated into the W3-B strain transformed with pKD46 vector. The recovered strain was streaked on LB plate medium containing 50 μg/L of kanamycin, followed by culture at 37° C. for overnight. Then, a strain exhibiting resistance was selected.

PCR was performed by using the selected strain as a template with primers of SEQ. ID. NO: 3 and NO: 4 under the same conditions as the above. The deletion of ThrB gene was identified by selecting the strain whose size is 1.6 kb on 1.0% agarose gel. The strain was then transformed with pCP20 vector and cultured in LB medium. The final thrB knock out strain was constructed in which the size of thrB gene reduced to 150 kb on 1.0% agarose gel by PCR under the same conditions. Kanamycin marker was confirmed to be eliminated. The constructed strain was named W3-BT.

<1-3> Deletion of MetJ Gene

To delete the metJ gene which is the regulator gene of the metA gene involved in methionine precursor synthesis, FRT one step PCR deletion was performed by the same manner as used for the deletion of metB gene.

To construct a metJ deletion cassette. PCR was performed with primers of SEQ. ID. NO: 5 and NO: 6 as follows; 30 cycles of denaturation at 94° C. for 30 seconds, annealing at 55° C. for 30 seconds, extension at 72° C. for 1 minute. The PCR product was electrophoresed on 1.0% agarose gel, followed by purification of DNA obtained from 1.2 kbp band. The recovered DNA fragment was electroporated into the W3-BT strain transformed with pKD46 vector. The recovered strain was streaked on LB plate medium containing chloramphenicol, followed by culture at 37° C. overnight. Then, a strain exhibiting resistance was selected.

PCR was performed by using the selected strain as a template with primers of SEQ. ID. NO: 7 and NO: 8 under the same conditions as the above. The deletion of metJ was identified by confirming the 1.6 kb sized gene on the 1.0% agarose gel. The strain was then transformed with pCP20 vector and cultured in LB medium. The final metJ knock out strain was constructed in which the size of metJ gene reduced to 600 kb on 1.0% agarose gel by PCR under the same conditions and the strain Chloramphenicol marker was confirmed to be eliminated. The constructed strain was named W3-BTJ.

<1-4> Deletion of MetA Gene

To increase the production of O-acetylhomoserine, metA gene encoding homoserine O-succinyltransferase was deleted in W3-BTJ strain. Based on the founding that metX gene integration resulted in the accumulation of both O-succinylhomoserine and O-Acetylhomoserine, it was expected that metA gene deletion resulted in the promotion of the accumulation of O-acetylhomoserine (Table 3). To delete the metA gene, FRT one step PCR deletion was performed.

To construct metA deletion cassette, PCR was performed with primers of SEQ. ID. NO: 9 and NO: 10 as follows; 30 cycles of denaturation at 94° C. for 30 seconds, annealing at 55° C. for 30 seconds, extension at 72° C. for 1 minute.

The PCR product was electrophoresed on 1.0% agarose gel. followed by purification of DNA obtained from 1.2 kbp band. The recovered DNA fragment was electroporated into the E. coli W3-BTJ strain transformed with pKD46 vector. The recovered strain was streaked on LB plate medium containing chloramphenicol, followed by culture at 37° C. for overnight. Then, a strain exhibiting resistance was selected.

PCR was performed by using the selected strain as a template with primers of SEQ. ID. NO: 9 and NO: 10 under the same conditions as the above. The deletion of metA gene was identified by confirming 1.1 kb sized gene on 1.0% agarose gel. The strain was then transformed with pCP20 vector and cultured in LB medium. The final metA knock out strain was constructed in which the size of metA gene reduced to 100 kb on 1.0% agarose gel by PCR under the same conditions. Chloramphenicol marker was confirmed to be eliminated. The constructed strain was named W3-BTJA.

<1-5> Overexpression of MetX Gene

To increase production of O-acetylhomoserine, overexpression of metX gene encoding homoserine O-acetyltransferase was performed.

PCR was performed by using chromosome of *Leptospira meyeri* as a template with primers of SEQ. ID. NO: 28 and NO: 29 as follows; 25 cycles of denaturation at 94° C. for 30 seconds, annealing at 55° C. for 30 seconds, extension at 72° C. for 2 minute.

The PCR product was electrophoresed on 1.0% agarose gel, followed by purification of DNA obtained from 1.1 kbp band. After isolation of the DNA fragment, vector pCL1920 containing CJ1 promoter was cleaved with the restriction enzyme EcoRV and ligated to the isolated DNA fragment. The E. coli was transformed with the vector and plasmid-carrying cells were selected on LB agar containing 50 μg/L of spectinomycin. The constructed vector was named pCJ1-MetXlme-CL. The vector was electroporated into W3-BTJ strain and the constructed strain was named W3-BTJ/pCJ-MetXlme-CL.

As another method of overexpressing of metX gene. PCR was performed by using chromosome of *Corynebacterium glutamicum* as a template with primers of SEQ. ID. NO: 30 and NO: 31 as follows; 25 cycles of denaturation at 94° C. for 30 seconds, annealing at 55° C. for 30 seconds, extension at 72° C. for 2 minute.

The PCR product was electrophoresed on 1.0% agarose gel, followed by purification of DNA obtained from 1.1 kbp band. After isolation of the DNA fragment, vector pCL1920 containing CJ1 promoter was cleaved with the restriction enzyme EcoRV and ligated to the isolated DNA fragment. The E. coli was transformed with the vector and plasmid-carrying cells were selected on LB agar containing 50 μg/L of spectinomycin. The constructed vector was named pCJ1-MetXlme-CL. The vector was electroporated into W3-BTJ strain and the constructed strain was named W3-BTJ/pCJ-MetXegl-CL.

As another method of overexpressing of metX gene, PCR was performed by using chromosome of *Deinococcus radiodurans* as a template with primers of SEQ. ID. NO: 11 and NO: 12 as follows; 25 cycles of denaturation at 94° C. for 30 seconds, annealing at 55° C. for 30 seconds, extension at 72° C. for 2 minute.

The PCR product was electrophoresed on 1.0% agarose gel, followed by purification of DNA obtained from 1.1 kbp band. After isolation of the DNA fragment, vector pCL1920 containing CJ1 promoter was cleaved with the restriction enzyme EcoRV and ligated to the isolated DNA fragment. The *E. coli* was transformed with the vector and plasmid-carrying cells were selected on LB agar containing 50 μg/L of spectinomycin. The constructed vector was named pCJ1-MetXdr-CL. The vector was electroporated into W3-BTJ strain and the constructed strain was named W3-BTJ/pCJ-MetXdr-CL.

As another method of overexpressing of metX gene, PCR was performed by using chromosome of *Mycobacterium smegmatis* as a template with primers of SEQ. ID. NO: 13 and NO: 14 as follows; 25 cycles of denaturation at 94° C. for 30 seconds, annealing at 55° C. for 30 seconds, extension at 72° C. for 2 minute.

The PCR product was electrophoresed on 1.0% agarose gel, followed by purification of DNA. After isolation of the DNA fragment, vector pCL1920 containing CJ1 promoter was cleaved with the restriction enzyme EcoRV and ligated to the isolated DNA fragment. The *E. coli* was transformed with the vector and plasmid-carrying cells were selected on LB agar containing 50 μg/L of spectinomycin. The constructed vector was named pCJ-MetXmsm-CL. The vector was electroporated into W3-BTJ strain and the constructed strain was named W3-BTJ/pCJ-MetXmsm-CL.

As another method of overexpressing of metX gene, PCR was performed by using chromosome of *Pseudomonas aeruginosa* PAO1 (pae) as a template with primers of SEQ. ID. NO: 15 and NO: 16 as follows: 25 cycles of denaturation at 94° C. for 30 seconds, annealing at 55° C. for 30 seconds, extension at 72° C. for 2 minute.

The PCR product was electrophoresed on 1.0% agarose gel, followed by purification of DNA. After isolation of the DNA fragment, vector pCL1920 containing CJ1 promoter was cleaved with the restriction enzyme EcoRV and ligated to the isolated DNA fragment. The *E. coli* was transformed with the vector and plasmid-carrying cells were selected on LB agar containing 50 μg/L of spectinomycin. The constructed vector was named pCJ-MetXpae-CL.

The above constructed vectors were electroporated into W3-BTJA strain respectively and production capacity of the strain was checked using flask culture as described in Example 2-1.

O-acetylhomoserine production of each strain is measured, based on 100% of O-acetylhomoserine production of strain introduced metX vector derived from *corynebacterium glutamicum* (PCT/KR2007/003650).

As a result, O-acetylhomoserine production capacity was significantly increased in the strains each transformed with vector pCJ-MetXdra-CL, pCJ-MetXmsm-CL and pCJ-MetXlme-CL.

|  | Plasmid | O-acetylhomoserine production (%) |
|---|---|---|
| W3BTJA | pCJ-metXcgl-CL | 100 |
|  | pCJ-metXmsm-CL | 114 |
|  | pCJ-metXlme-CL | 105 |
|  | pCJ-metXpae-CL | 100 |
|  | pCJ-metXdra-CL | 164 |

For the stable expression of the metX gene from *D. radiodurans* (metX(dra)) showing the most efficient production among the above three, the metX(dra) gene was inserted into the chromosome of *E. coli*. pSG vector system was used to construct metX(dra)-inserting strain (Appl. Environ. Microbiol. 1993 V 59. p. 3485-3487, Villaverde. A et. al).

First of all, 600 bp of upstream region of the metA from genomic DNA was PCR-amplified with primers of SEQ. ID. NO: 17 and NO: 18, and 600 bp of downstream region of the metA from genomic DNA was PCR-amplified with primers of SEQ. ID. NO: 19 and NO: 20. Then, the metX(dra) was PCR-amplified with primers of SEQ. ID. NO: 21 and NO: 22. Each PCR fragment was isolated by gel-elution and the fragment mixture was PCR-amplified with primers of SEQ. ID. NO: 23 and NO: 24. The amplified DNA cleaved with the restriction enzyme BamHI/EcoRI and cloned into pSG76C vector. W3-BTJA strain was transformed with the above constructed vector and chloramphenichol-resistant strains were selected and successful cloning of metX dra gene was detected. The detected strains were transformed with pIsceI vector to removing marker, and reselected. As a result of confirming O-acetylhomoserine production capacity, the production of the metX(dra) gene-introduced strain was similar to that strain harboring pCL-metXdra plasmid.

<1-6> Overexpression of ThrA Gene

To increase production of O-acetylhomoserine more efficiently, overexpression of thrA gene was performed.

For this, thrA gene was PCR-amplified by using chromosome of *E. coli* CJM002 (KCCM10568), the L-threonine producing strain, as a template with primers of SEQ. ID. NO: 25 and NO: 26. The amplified DNA fragment was isolated by gel-elution and ligated with CJ1 promoter in pCL1920 vector using the restriction enzyme EcoRV. The ligated vector was named pCJ-thrA(M)-CL and transformed into the strains which manufactured by method of Example 1-1)~1-5. The amino acid sequence coding by the thrA gene is represented in SEQ. ID. NO: 27 that has a mutation in amino acid position 345.

<1-7> Converting of L-Threonine Producing Strain

O-acetylhomoserine producing strain was constructed using *E. coli* CJM002 (KCCM10568) which is the L-threonine producing and L-methionine-independent strain, as described in Example 1-1 to 1-5, and named as CJM-X. The chromosome of CJM-X strain has the metX gene derived from *D. radiodurans*. And another L-methionine precursor producing strain was constructed using FTR2533 (KCCM10541) which is the L-threonine producing strain disclosed in PCT/KR2005/00344, as described in Example 1-1 to 1-5, and named as CJM-2X. The chromosome of CJM-2X strain has the metX gene derived from *D. radiodurans*. Each strain was transformed with the thrA expression vector as described in Example 1-6 and production of methionine precursor was measured in this strain.

Example 2

Fermentation for the Production of L-Methionine Precursor

<2-1> Experiment of Flask Culture

To investigate the methionine precursor production capacity of the strain constructed in Example 1, Erlenmeyer flask culture was performed. CJM2-BTJA transformed with metX expression vector and CJM-X, CJM2-X, CJM2-X/pthrA(M)-CL were cultured on LB plate media at 31° C. for overnight. The *Escherichia coli* CJM-BTJA (pCJ-MetX-CL) described in PCT/KR2007/003650. O-acetylhomoserine precursor-producing strain, was deposited on Jul. 5, 2007, with the accession No. KCCM-10873.

A single colony was inoculated in 3 ml of LB medium containing spectinomycin, followed by culture at 31° C. for 5 hours. The culture solution was 200 fold diluted in 250 ml Erlenmeyer flask containing 25 ml of methionine precursor producing medium, followed by culture at 31° C., 200 rpm for 64 hours. HPLC was performed to compare with methionine precursor production capacity (Table 2 and Table 3). As a result, methionine production capacity was significantly increased in the methionine precursor-producing strain prepared from the L-threonine producing strain free from the requirement for methionine.

TABLE 1

Flask medium composition for methionine precursor production

| Composition | Concentration (per liter) |
|---|---|
| Glucose | 40 g |
| Ammonium sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.15 g |
| Threonine | 0.15 g |

TABLE 2

Methionine precursor (O-acetylhomoserine) production by flask culture

| | O-acetylhomoserine (g/L) |
|---|---|
| CJM-BTJA/pCJ-metXdr-CL | 15 |
| CJM-X | 14 |
| CJM2-X | 18.3 |
| CJM2-X/pthrA(M)-CL | 20.7 |

<2-2> Large Scale Fermentation

A few strains exhibiting O-acetylhomoserine production capacity was selected and cultured in a 5 L fermentor to mass-produce O-acetylhomoserine. Each strain was inoculated in LB medium containing spectinomycin, followed by culture at 31° C. for overnight. Then, a single colony was inoculated in 10 ml LB medium containing spectinomycin, which was cultured at 31° C. for 5 hours. The culture solution was 100 fold diluted in 1000 ml Erlenmeyer flask containing 200 ml of methionine precursor seed medium, followed by culture at 31° C., 200 rpm for 3-10 hours. The culture solution was inoculated in a 5 L fermentor, followed by further culture for 20-100 hours by fed-batch fermentation. The methionine precursor concentration in the fermented solution was measured by HPLC and the results are shown in Table 4.

TABLE 3

Fermentor medium composition for methionine precursor production

| Composition | Seed media | Main media | Feed media |
|---|---|---|---|
| Glucose(g/L) | 10.1 | 40 | 600 |
| $MgSO_4 7H_2O$(g/L) | 0.5 | 4.2 | |
| Yeast extract(g/L) | 10 | 3.2 | |
| $KH_2PO_4$ | 3 | 3 | 8 |
| Ammonium sulfate(g/L) | | 6.3 | |
| $NH_4Cl$(g/L) | 1 | | |
| NaCl(g/L) | 0.5 | | |
| $Na_2HPO_4 12H_2O$(g/L) | 5.07 | | |
| DL-Methionine(g/L) | | 0.5 | 0.5 |
| L-Isoleucine(g/L) | 0.05 | 0.5 | 0.5 |
| L-Threonine(g/L) | | 0.5 | 0.5 |

TABLE 4

Methionine precursor production in a fermentor

| | O-acetylhomoserine (g/L) |
|---|---|
| CJM-BTJA/pCJ-metXcgl-CL | >55 |
| CJM-BTJA/pCJ-metXdra-CL | >75 |
| CJM-X/pthrA(M)-CL | >80 |
| CJM2-X/pthrA(M)-CL | >90 |

INDUSTRIAL APPLICABILITY

As described hitherto, using the methionine precursor producing strain in present invention, methionine can be produced environment-friendly than conventional chemical methionine synthetic method. And the L-methionine converted from O-acetylhomoserine produced from the strain according to the present invention can be widely used in the production of animal feed or animal feed additives, in addition to human food or food additives.

We claim:

1. A microorganism for producing O-acetylhomoserine, wherein:
   a) a homoserine O-acetyltransferase activity (EC2.3.1.31) is introduced and enhanced; and
   b) an aspartokinase or homoserine dehydrogenase activity (EC2.7.2.4 or 1.1.1.3) is enhanced,
   wherein the microorganism is an *Escherichia* sp, and the homoserine O-acetyltransferase is encoded by a gene from *Deinococcus radiodurans*.

2. The microorganism of claim 1, wherein the homoserine O-acetyltransferase has the amino acid sequence of Unipro database No. Q9RVZ8 (SEQ ID NO: 32).

3. The microorganism of claim 1, wherein the aspartokinase or homoserine dehydrogenase peptide has a mutation at amino acid position 345.

4. The microorganism of claim 1, wherein the aspartokinase or homoserine dehydrogenase peptide has SEQ ID NO: 27.

5. The microorganism of claim 1, wherein the microorganism is an *Escherichia coli*.

6. The microorganism of claim 1, wherein the microorganism is derived from L-threonine, L-isoleucine or L-lysine producing strain.

7. The microorganism of claim 1, wherein the activity of homoserine kinase is reduced, inhibited, or inactivated.

8. The microorganism of claim 1, wherein a transcription regulator of methionine synthetic pathway is weakened or inactivated.

9. The microorganism of claim 1, wherein the microorganism is derived from the threonine producing strain *Escherichia coli* MF001 free from methionine-dependency (Accession No. KCCM 10568).

10. The microorganism of claim 1, wherein the microorganism is derived from the threonine producing strain *Escherichia coli* FTR2533 (Accession No. KCCM 10541).

11. The microorganism of claim 1, wherein the microorganism is *Escherichia coli* having Accession No. KCCM 10921P.

12. The microorganism of claim 1, wherein the microorganism is *Escherichia coli* having Accession No. KCCM 10925P.

13. The microorganism of claim 1, wherein a biosynthetic pathway of threonine is suppressed.

14. The microorganism of claim 1, wherein expression of endogenous homoserine O-succinyltransferase encoded by metA gene, endogenous cystathionine gamma synthase encoded by metB gene, endogenous transcription regulator of methionine synthetic pathway encoded by metJ gene, endogenous O-acetylhomoserine sulfhydrylase encoded by metY gene, endogenous O-succinylhomoserine sulfhydrylase encoded by metZ gene, endogenous homoserine kinase encoded by thrB gene, or a combination thereof, is suppressed.

15. The microorganism of claim 1, wherein a gene expression of thrA is enhanced.

16. A method of producing O-acetylhomoserine, comprising;
a) culturing the microorganism of claim 1; and
b) isolating O-acetylhomoserine.

17. A method of producing O-acetylhomoserine, comprising;
a) fermenting the microorganism of claim 1; and
b) enriching the O-acetylhomoserine in the medium or in the microorganism.

18. The microorganism of claim 1, wherein the activity of cystathionine gamma synthase is reduced, inhibited, or suppressed.

19. The microorganism of claim 1, wherein the gene expression of metB encoding the cystathionine gamma synthase is suppressed.

20. The microorganism of claim 1, wherein the gene expression of thrB encoding the homoserine kinase is suppressed.

21. The microorganism of claim 1, wherein the gene expression of metJ is suppressed.

* * * * *